(12) United States Patent
Peyman

(10) Patent No.: US 8,119,165 B2
(45) Date of Patent: *Feb. 21, 2012

(54) METHOD AND COMPOSITION FOR HYPERTHERMALLY TREATING CELLS

(76) Inventor: Gholam A. Peyman, Sun City, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/189,606

(22) Filed: Jul. 25, 2011

(65) Prior Publication Data

US 2011/0287035 A1 Nov. 24, 2011

Related U.S. Application Data

(60) Continuation-in-part of application No. 13/149,209, filed on May 31, 2011, which is a continuation-in-part of application No. 12/478,029, filed on Jun. 4, 2009, now Pat. No. 7,964,214, which is a continuation-in-part of application No. 11/485,352, filed on Jul. 13, 2006, now Pat. No. 7,638,139, which is a division of application No. 10/073,863, filed on Feb. 14, 2002, now Pat. No. 7,101,571.

(51) Int. Cl.
*A61F 13/00* (2006.01)
*A61K 9/14* (2006.01)

(52) U.S. Cl. ........................... 424/489; 424/422

(58) Field of Classification Search .................. None
See application file for complete search history.

(56) References Cited

U.S. PATENT DOCUMENTS

| | | | |
|---|---|---|---|
| 3,993,754 A | 11/1976 | Rahman et al. | |
| 4,235,871 A | 11/1980 | Papahadjopoulos et al. | |
| 4,522,803 A | 6/1985 | Lenk et al. | |
| 4,586,512 A | 5/1986 | Do-huu et al. | |
| 4,620,546 A | 11/1986 | Aida et al. | |
| 4,658,828 A | 4/1987 | Dory | |
| 4,891,043 A | 1/1990 | Zeimer et al. | |
| 5,094,854 A | 3/1992 | Ogawa et al. | |
| 5,149,319 A | 9/1992 | Unger | |
| 5,203,782 A * | 4/1993 | Gudov et al. | 606/31 |
| 5,935,942 A | 8/1999 | Zeimer | |
| 5,976,502 A | 11/1999 | Khoobehi et al. | |
| 6,197,022 B1 | 3/2001 | Baker | |
| 6,248,727 B1 | 6/2001 | Zeimer | |
| 7,638,139 B2 * | 12/2009 | Peyman | 424/450 |

* cited by examiner

*Primary Examiner* — Susan Tran
(74) *Attorney, Agent, or Firm* — Thompson Hine LLP

(57) ABSTRACT

A method and composition for hyperthermally diagnosing and monitoring treatment of cells in an animal with photoacoustic sound and nanoparticles. The heat (temperature) and photoacoustic sound wave production inside the target tissue is measured. The desired temperature is achieved using a laser and photoacoustic imaging technique. Hyperthermia treatment of tissue in a target site applies a heat source to kill cells without protein denaturation. The method introduces an encapsulated dye that is released at a selected temperature in the target site to indicate that a threshold temperature has been reached to hyperthermally treat the tissue. In one embodiment, the composition releases the dye at a temperature of 42° C. to 56° C., and preferably about 45° C. to 49° C. The composition which can be a liposome composition encapsulating the dye can be introduced to the bloodstream of the patient to flow through the target site.

3 Claims, 1 Drawing Sheet

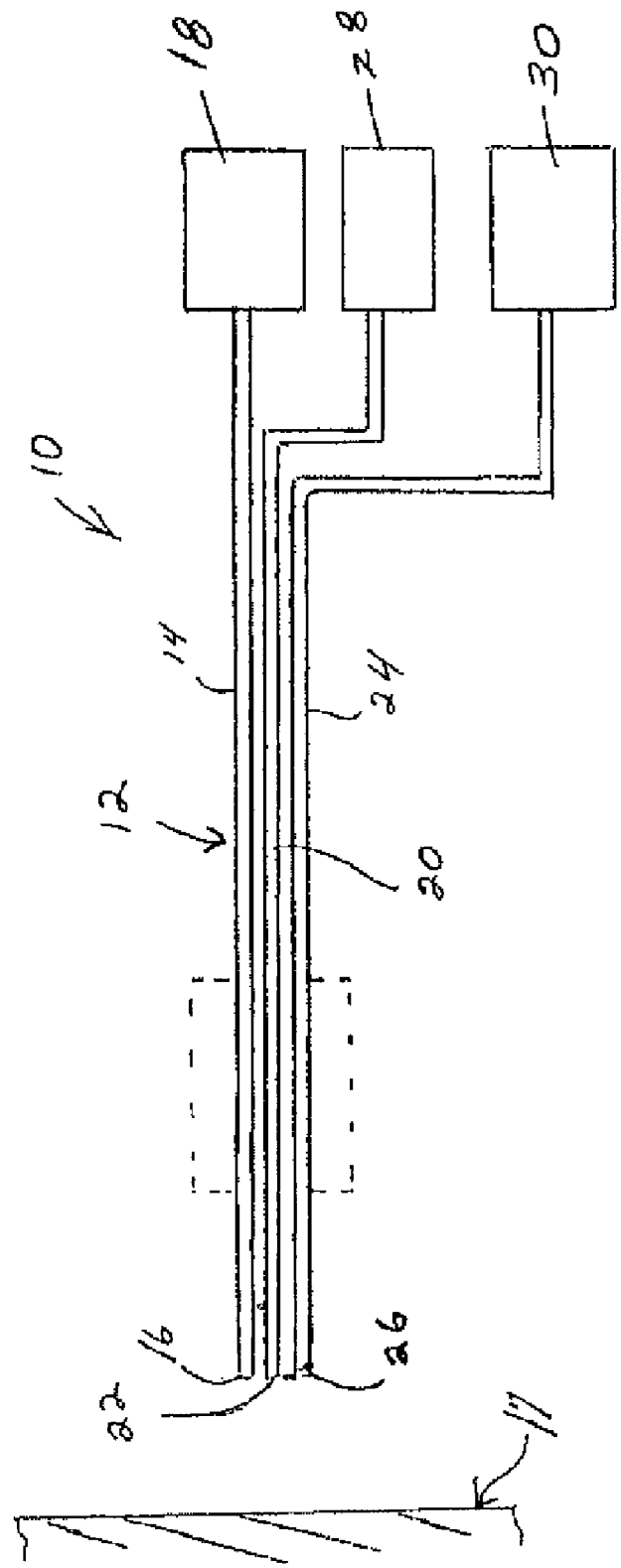

METHOD AND COMPOSITION FOR HYPERTHERMALLY TREATING CELLS

This application is a Continuation-in-Part of co-pending U.S. patent application Ser. No. 13/149,209 filed May 31, 2011; which is a Continuation-in-Part of U.S. patent application Ser. No. 12/478,029 filed Jun. 4, 2009 now U.S. Pat. No. 7,964,214; which is a Continuation-in-Part of U.S. patent application Ser. No. 11/485,352 filed Jul. 13, 2006 now U.S. Pat. No. 7,638,139; which is a Division of U.S. patent application Ser. No. 10/073,863 filed Feb. 14, 2002 now U.S. Pat. No. 7,101,571; the entirety of each is hereby expressly incorporated by reference herein.

FIELD OF THE INVENTION

The present invention relates to a method and composition for hyperthermally treating cells at a site in the body. More particularly, the present invention relates to a method for treating cells at a target site in the body, such as at a lens capsule of an eye, tumors, and exudative ARM (age related macular degeneration) by applying thermal energy to the target site to heat the cells to a temperature which will kill the cells or impede cell multiplication without exceeding the protein denaturation temperature of the tissue.

BACKGROUND OF THE INVENTION

Several techniques currently exist for treating cells at a selected site in the body with heat or chemicals to kill or impede multiplication of those cells to prevent undesired cell proliferation. For example, numerous types of chemotherapy drugs exists which, when injected into a tumor or delivered systemically to a patient, attack and kill cancerous cells to prevent them from further multiplying.

Radiation techniques can also be used to kill cancerous or other undesired cells. Cell death begins to occur when the cells are heated to a temperature of about 5° C. or more above the normal body temperature of 37° C. Applying radiation to a localized site in the body, such as a tumor or other area containing undesired cells, can heat the cells at the site to temperatures in excess of 60° C. Such high temperatures causes a phenomenon known as protein denaturation to occur in the cells, which results in immediate cell death. Accordingly, radiation therapy has been suitable in successfully treating certain types of cancers and other diseases involving uncontrolled cell growth.

Other types of heating techniques, such as the use of probes or catheters to provide localized heat to a site of interest also exist. Like radiation therapy, these techniques also heat the cells to a temperature sufficient to cause protein denaturation in the cells to thus kill the cells quickly.

Photosensitive chemicals are also used to kill cells at certain sites of interest in the body. For example, a photosensitive chemical can be injected directly into a site of interest to expose cells at that site to the chemical. A light emitting source, which emits light at a wavelength that will activate the photosensitive chemical, is then focused on the site of interest. Accordingly, the light activates the photosensitive chemical that has been absorbed by or is otherwise present in the cells of interest. The activated chemical kills the cells, which thus prevents undesired cell proliferation.

Although the techniques mentioned above can be suitable for preventing certain types of cell proliferation and certain sites in the body, several drawbacks with these techniques exist. For example, often the use of chemotherapy drugs alone to treat a tumor or cancerous site is insufficient to kill the undesired cells. Moreover, the chemotherapy drugs also kill many normal healthy cells along with the cancerous cells, which can adversely affect the patient's health.

The use of radiation in conjunction with chemotherapy can have a more detrimental effect on the cancerous cells. However, as with chemotherapy, radiation often kills normal healthy cells, such as those in front of or behind the site of interest, along with the cancerous cells. Moreover, the intense heating of the cells can cause the cells to coagulate and thus block the capillaries at the site of interest. The blocked capillaries therefore prevent chemotherapy drugs from reaching the site of interest.

One example of a method of chemically treating a target site is disclosed in U.S. Pat. No. 6,248,727 to Zeimer. This method delivers a liposome containing a fluorescent dye and tissue-reactive agent. The liposome is administered intravenously to flow to the locus in the eye of the patient and the site is non-invasively heated to release the dye and the tissue-reactive agent. The dye is fluoresced to observe the pattern of the fluorescence. The tissue-reactive agent is activated to chemically damage and occlude the blood vessel. The liposomes are selected to release the dye at a temperature of 41° C. or less without causing thermal damage to the blood vessel.

In addition, the above techniques have not been used to prevent unwanted cell proliferation at certain locations in the eye, such as at the retina or at the lens capsule. Because the retina is very sensitive, conventional radiation techniques can be too severe to treat cancerous cells on, in or under the retina.

Also, after cataract surgery, a phenomenon known as capsular opacification and, in particular, posterior capsular opacification can occur in which the epithelial cells on the lens capsule of the eye experience proliferated growth. This growth can result in the cells covering all or a substantial portion of the front and rear surfaces of the lens capsule, which can cause the lens capsule to become cloudy and thus adversely affect the patient's vision. These cells can be removed by known techniques, such as by scraping away the epithelial cells. However, it is often difficult to remove all of the unwanted cells. Hence, after time, the unwanted cells typically will grow back, thus requiring further surgery.

Accordingly, a need exists for a method for hyperthermally treating tissue and preventing unwanted cell proliferation at sites in the body, especially at sites in the eye such as the retina, choroid and lens capsule, which does not suffer from the drawbacks associated with the known techniques discussed above.

SUMMARY OF THE INVENTION

The present invention is directed to a method of hyperthermally treating tissue by heating the tissue above a temperature which kills cells in the tissue. In particular, the invention is directed to a method of heating tissue above a temperature effective to treat the tissue without denaturing the protein. The present invention also relates to a method and composition for hyperthermally treating cells in the eye with simultaneous imaging.

Accordingly, a primary aspect of the invention is to provide a method for heating tissue at least to a temperature sufficient to hyperthermally treat the tissue.

Another aspect of the invention is to provide a method of hyperthermally treating tissue to a temperature sufficient to kill cells in the tissue and at a temperature below the protein denaturization temperature of the tissue.

A further aspect of the invention is to provide a method of hyperthermally treating tissue, where the tissue includes or is provided with a temperature indicator to indicate a hyperthermally effective temperature of the tissue.

Still another aspect of the invention is to provide a method of hyperthermally treating tissue where a temperature indicator composition is introduced into the tissue or bloodstream near the tissue to indicate a tissue temperature effective to hyperthermally treat the tissue and a temperature indicator to indicate a tissue temperature above a protein denaturization temperature of said tissue.

A further aspect of the invention is to provide a method of hyperthermally treating tissue by introducing a temperature indicator into the tissue and heating the tissue to a temperature where the temperature indicator can be detected. In a preferred embodiment, the temperature at which the indicator can be detected is a temperature effective to hyperthermally treat the tissue and is at a temperature below the protein denaturization temperature.

A further aspect of the invention is to provide a method of heating and detecting a temperature of a tissue between a first temperature and a second temperature. The method introduces a temperature indicator into the tissue. The temperature indicator includes a first dye that can be detected at the first temperature to indicate that the first temperature has been reached, and a second dye that can be detected at the second temperature to indicate that the second temperature has been reached.

Still another aspect of the invention is to provide a temperature indicating composition for introducing into a tissue to be thermally treated. The composition includes a first dye encapsulated in a heat sensitive liposome where the first dye is releasable at a temperature effective to hyperthermally treat the tissue and at a temperature below the protein denaturization temperature. The composition also includes a second dye encapsulated in a second liposome where the second dye is releasable at a temperature at or above the protein denaturization temperature.

Another aspect of the invention is to provide a method to hyperthermally treat tissue to kill the tissue cells substantially without protein denaturization of the tissue where the tissue includes a heat sensitive liposome containing a temperature indicating dye and a temperature activated bioactive compound. The tissue is heated to release the dye from the liposome to indicate a thermally effective temperature to kill cells in the tissue at a temperature below the protein denaturization temperature. The heat applied to the tissue simultaneously releases the bioactive compound to treat the tissue.

The various aspects of the invention are basically attained by providing a method of hyperthermally treating tissue in an animal. The method comprises the step of introducing a temperature indicating substance into the bloodstream of the animal to flow through a target site. The temperature indicating substance includes a fluorescent dye encapsulated within a heat sensitive liposome. The fluorescent dye is releasable from the liposome at a temperature of at least 41° C. A heat source is applied to the target site and the target is hyperthermally heated to at least 41° C. to release and fluoresce the dye and to hyperthermally treat the target site for a time sufficient to kill cells in the tissue.

The aspects of the invention are also attained by providing a method of detecting a threshold temperature and of hyperthermally treating tissue in an animal. The method comprises the step of introducing a first fluorescent dye encapsulated in a first heat sensitive liposome into the bloodstream of an animal in a location to flow through a target site in the animal. The first fluorescent dye is releasable from the first heat sensitive liposome at a temperature of at least 41° C. The target site is heated to a temperature to release the first fluorescent dye and the first fluorescent dye is fluoresced to indicate and visualize a tissue temperature of at least 41° C. Heating of the target site is continued at a temperature of at least 41° C. for a time sufficient to hyperthermally treat the tissue.

The aspects of the invention are further attained by providing a method of hyperthermally treating tissue of an animal. The method comprises the step of introducing a temperature indicating substance into the bloodstream of the animal to flow through a target site. The temperature indicating substance includes a first fluorescent dye encapsulated in a first temperature sensitive liposome. The first fluorescent dye is releasable from the first liposome by heating to a temperature of at least 42° C. A second fluorescent dye encapsulated in a second temperature sensitive liposome is also included. The second fluorescent dye is releasable from the second liposome by heating to a temperature of at least 50° C. The target site is heated to a temperature of at least 42° C. The first fluorescent dye is fluoresced to indicate an effective temperature for hyperthermally treating the tissue without releasing the second fluorescent dye from the second liposomes.

These and other aspects of the invention will become apparent to one skilled in the art in view of the following detailed description of the invention.

BRIEF DESCRIPTION OF THE DRAWINGS

The FIGURE is a schematic diagram of one embodiment of the invention showing a probe for hyperthermally treating tissue and visualizing a dye in the target site.

DETAILED DESCRIPTION OF THE INVENTION

The present invention is directed to a method and composition for hyperthermally treating tissue. In particular, the invention is directed to as method for heating tissue above a temperature effective to kill tissue cells or inhibit multiplication of cells below the protein denaturization temperature of the tissue.

The method of the invention introduces a composition into the bloodstream of the body in a location to flow into or through a target site to be treated. A heat source such as generated by radiation energy is applied to the target site to heat the tissue in the target site for a time sufficient to hyperthermally treat the tissue and activate the composition. As used herein, the term "hyperthermal" refers to a temperature of the cell or tissue that kills or damages the cells without protein denaturization.

The composition contains a temperature indicator that is able to provide a visual indication when a minimum or threshold temperature is attained that is sufficient to hyperthermally treat the tissue. It is a feature of the invention to provide a method of heating tissue in a target site to a hyperthermally effective temperature and to provide a visual indication that a temperature of at least 41° C., and preferably at least 42° C. is attained. In one embodiment, the composition includes a second temperature indicator to provide a visual indication when a protein denaturization temperature is attained thereby providing an indication that a maximum desired temperature is exceeded. The heat source can be applied to the tissue so that the composition provides an indication that a thermally effective temperature is attained that is below the protein denaturization temperature of the tissue.

In one embodiment of the invention, the method introduces a composition to a target site, where the composition includes a fluorescent dye that is encapsulated in a heat sensitive particle, such as a liposome. The dye is a fluorescent dye that can be excited to fluoresce and be observed or visualized by the operator. Preferably, the heat sensitive liposomes are formed to rupture or release the fluorescent dye at a temperature at least equal to the temperature necessary to kill cells in the tissue and at a temperature below the protein denaturization temperature. The composition containing the heat sensitive liposomes encapsulating the fluorescent dye is introduced into the bloodstream to flow to or through the target site. The amount of the liposome composition is introduced in an amount effective to be released in or near the target site and to excited and visualized by the exciting light source and the visualizing device. The composition containing the dye can be injected in a single dose into the bloodstream or injected continuously to supply a continuous flow of the composition through the target site. The amount of the composition introduced can vary depending on the target site and the length of time that the dye is to be excited. A light or energy source is continuously applied to the target site to excite the dye and to cause the dye to fluoresce when released from the liposomes. An imaging device is used to capture the fluorescing light from the dye to provide a visual indication that the dye is released. The release temperature of the liposomes are selected to release the dye at a predetermined temperature so that when the dye is fluoresced and visualized, the visualization provides the operator with an indication that the release temperature in the target site has been attained. In one embodiment, the liposome composition is injected into the blood stream so that the composition is able to provide a continuous supply of the dye for fluorescing during the hyperthermal treatment. In this manner the operator is provided with a continuous indication that a sufficient temperature is being maintained.

The method of the invention is primarily directed to a method of heating tissue and cells in the tissue of an animal, particularly a human patient, at least to the temperature sufficient to kill or damage the cells. Cell death or cell damage is known to occur when the tissue cells are heated to a temperature of about 5° C. above the normal body temperature of 37° C. Therefore, the method of the invention heats the cells in the tissue to a temperature of about 41° C., and preferably at least 42° C. for a time sufficient to kill or damage the cells. Preferably, the heat source is applied to minimize unnecessary damage to the surrounding cells and tissue.

In one embodiment of the invention, the tissue is heated to a temperature of at least 41° C. and preferably in the range of at least about 42° C. to about 50° C. Heating the tissue to at least 42° C. ensures that a sufficient temperature is obtained to thermally treat the tissue and the cells effectively. Preferably, the tissue is heated to a temperature below the protein denaturization temperature of the tissue. Protein denaturization begins to occur at about 50° C. to 51° C. and occurs rapidly at temperatures of about 60° C. Preferably, the tissue is heated to a temperature of less than 60° C. and more preferably to a temperature of about 50° C. or less.

In one preferred embodiment, the tissue and the cells are heated to a temperature of about 47° C. to about 49° C. for a time sufficient to kill or damage the cells without protein denaturization. The length of time that the tissue is heated will depend on the location of the target site, the size and dimensions of the target site, the desired depth of penetration of the heat and the desired extent of thermal treatment- or damage of the tissue and cells in the target site. Typically, the heat source is applied for several minutes. In one embodiment, the heat source is applied for about 1 to 15 minutes, and typically about 5 to 10 minutes.

The heat source can be applied to a variety of the areas in the body where the hyperthermal treatment is desired. The target site can be tumors, organs, muscles and soft tissue. Examples of a target site include blood vessels and arteries, esophagus and eyes. In one embodiment, the method is suitable for hyperthermally treating the epithelial cells on the lens of the eye after cataract surgery. Other target sites include the retina and the choroid.

In other embodiments the target site may be cell components of various organs. The organs may be healthy or may contain tumors, either malignant or benign. The following are representative, not limiting, examples of cell components on which the inventive method may be applied: tumors of the central nervous system (CNS), various layers of skin and its underlying support structures, intestinal tract, kidney, urinary tract, female and male reproductive system organs, bone including bone marrow, circulatory system components including the heart, blood vessels, and circulating malignant cells, the lymphatic system including lymph nodes and vessels, and the respiratory system.

The target site is heated to the desired temperature to hyperthermally treat the target site using standard heating instruments and equipment for heating tissue and standard equipment for visualizing the dye in the target site that has been released from the heat sensitive particles. For example, the heating equipment preferably includes suitable heat or energy source that is able to focus the heat or energy on the target and is able to control heat and temperature of the tissue. The heat source can be an electrical resistance heating element, or an indirectly heated element. The heating device can also have a radiation energy source for producing heat at the target site, such as a radio frequency (RF) device, ultrasonic generators, laser, or infrared device. One example of an RF generator device for hyperthermally treating tissue in a selected target site is disclosed in U.S. Pat. No. 6,197,022, which is hereby incorporated by reference in its entirety. Examples of suitable ultrasonic devices for delivering ultrasonic hyperthermia are disclosed in U.S. Pat. Nos. 4,620,546, 4,658,828 and 4,586,512, the disclosures of which are hereby incorporated by reference in their entirety. In one embodiment, the duration of the applied radiation energy may be from about a femtosecond to about 15 minutes. In one embodiment, the duration of the applied radiation energy may be from about one picosecond to about 15 minutes. In one embodiment, the duration of the applied radiation energy may be from about one nanosecond to about 15 minutes. In one embodiment, the duration of the applied radiation energy may be from about one microsecond to about 15 minutes. In one embodiment, the duration of the applied radiation energy may be from about 1 second to about 15 minutes. In one embodiment, the duration of the applied radiation energy may be from about 1 second to about 15 seconds. In one embodiment, the temperature at which the radiation energy is applied ranges between about 45° C. to about 49° C. In one embodiment, the temperature at which the radiation energy is applied ranges between about 45° C. to about 56° C. For example and without limitation, relatively brief treatment times are used for circulating cells (e.g., cells in vessels of the circulatory and lymphatic systems). Relatively longer laser pulses may also be used for tissues located deep inside the body. In one embodiment, the ultrasound frequency can range between 0.5 KHz to 200 MHz. In one embodiment, the ultrasound frequency can range between 0.5 MHz to 10 MHz. In one embodiment, the ultrasound frequency can range between 10 MHz to 30 MHz. In one embodiment, the ultrasound frequency can range between 5 MHz to 80 MHz.

In one embodiment, the heat source includes a probe having a tip with the heating element or energy emitting element attached thereto. The energy emitting element can be an optical fiber operatively connected to a laser, infrared or ultraviolet light source. The probe preferably includes a suitable control mechanism for manipulating the probe to the target site and a control for controlling the energy applied to the target site. In one embodiment the wavelength of light is selected to be in the range between 350 nm to 1300 nm. In another embodiment the wavelength of light is selected to be in the range between 450 nm to 600 nm.

A suitable device for hyperthermally treating the tissue in a target site is shown in the FIGURE. The device 10 includes a probe 12 having an optical fiber 14 with a distal end 16 for emitting a laser light to heat the tissue 17. Preferably, the end 16 of optical fiber 14 can focus the light source on the target site 17. Optical fiber 14 is connected to laser generator 18 that is able to generate a laser beam of sufficient intensity and within wavelength for hyperthermally treating tissue. For use of the method in making a diagnostic assessment or for therapy, the tissue is treated to a temperature of at least 41° C. to 56° C., and preferably at least 42° C. to 56° C. In a preferred embodiment, probe 12 includes a second optical fiber 20 having a distal end 22 and a third optical fiber 24 having a distal end 26. Optical fiber 20 is operatively connected to a light source 28, such as a laser, that is able to emit a light beam having a wavelength capable of fluorescing a fluorescent dye in the target area when the dye is released from the heat sensitive particles. Optical fiber 24 is operatively connected to a suitable imaging device 30 for capturing the fluoresced light from the excited dye and visualizing and producing an image of the fluorescing dye in the target site. Imaging device 30 can be a CCD or a device equivalent to a funduscope. An example of a suitable funduscope is disclosed in U.S. Pat. No. 4,891,043 to Zeimer, which is hereby incorporated by reference in its entirety.

In another embodiment of the invention, the probe can include a heating element or a device for receiving a heated fluid that can transfer the heat to the tissue in the target site. The probe can include an expandable bladder member for receiving a heated fluid delivered from a fluid-heating source. In still another embodiment, the expandable bladder includes a permeable portion so that the heated fluid can be applied directly to the target site. A suitable aspirating device is preferably included to remove the excess heating fluid when applied directly to the target site.

In one embodiment, the target site is the retina or choroid in the eye of the patient. The heating and visualizing instrument includes a laser capable of focusing a laser beam on the target site where the laser beam has a wavelength and intensity to heat the cells to a temperature of at least 42° C. In one embodiment, the laser heats the cells to a temperature of 50° C. or below and preferably to about 42° C. to 56° C. The instrument also includes or is used in combination with a funduscope to excite or fluoresce the dye that has been released in the target site to capture and visualize the fluorescing dye. A funduscope that can be used is disclosed in U.S. Pat. No. 6,248,727, which is hereby incorporated by reference in its entirety. The laser source is selected to provide sufficient energy to heat the tissue in the target site to the desired temperature.

The fluorescent dye is encapsulated in a suitable heat sensitive particle and introduced into the patient in a location to be visualized in the target site. The heat sensitive particles can be microcapsules, or nanocapsules that are able to release the dye at a temperature of about 41° C., and preferably 42° C. or higher. In preferred embodiments, the fluorescent dyes are incorporated into heat sensitive liposomes that have a phase transition temperature at the temperature of hyperthermia. In one embodiment, the liposomes have a phase transition temperature within the desired temperature range that tissue or cells are to be heated.

In one embodiment, the liposomes have a phase transition temperature of at least 41° C. and preferably at least 42° C. In a preferred embodiment, the liposomes have a phase transition temperature of about 45° C. to about 50° C.

The liposomes can be made by various processes as known in the art. The phase transition temperature of the phospholipid is selected to control the temperature that the dye and other components are released from the liposomes. Phospholipids are known to have different phase transition temperatures and can be used to produce liposomes having release temperatures corresponding to the phase transition of the phospholipids. Suitable phospholipids include, for example, dimyristoylphosphatidyl choline having a phase transition temperature of 23.9° C., palmitoylmyristoylphosphatidyl choline having a phase transition temperature of 27.2° C., myristolypalmitoylphosphatidyl choline having a phase transition temperature of 35.3° C., dipalmitoylphosphatidyl choline having a phase transition temperature of 41.4° C. stearoylpalmitoylphosphatidyl choline having a phase transition temperature of 44.0° C., palmitoylstearolyphosphatidyl choline having a phase transition of 47.4° C., and distearoylphosphatidyl choline having a phase transition temperature of 54.9° C. Another suitable phospholipid is a synthetic $C_{17}$ phosphatidyl choline from Aventi Inc. having a phase transition temperature of about 48° C.-49° C.

The phase transition temperature and the release temperature of the liposomes can be selected by combining the different phospholipids during the production of the liposomes according to the respective phase transition temperature. The phase transition of the resulting liposome membrane is generally proportional to the ratio by weight of the individual phospholipids. Thus, the composition of the phospholipids are selected based on the respective phase transition temperature so that the phase transition temperature of the liposome membrane will fall within the selected range. By adjusting the phase transition temperature of the liposome membrane to the selected range, the temperature at which the liposomes release the dyes and other components can be controlled during hyperthermia.

The liposomes in one embodiment of the invention are preferably prepared so that the liposome membrane has a phase transition temperature of at least 42° C., and preferably about 42° C. to about 50° C. In a preferred embodiment, the liposomes leak or rupture at a temperature of about 49° C. or less, and typically between about 45° C. and 49° C. In one embodiment, the phospholipids have saturated acyl groups. For example, glycerophospholipids can be used that have two acyl groups having 8 or more carbon atoms and where at least one of the acyl groups have at least 10 carbon atoms and typically 12-18 carbon atoms. Examples of suitable phospholipids include hydrogenated lecithin from plants and animals, such as egg yolk lecithin and soybean lecithin. The phospholipid can also be phosphatidyl choline produced from partial or complete synthesis containing mixed acyl groups of lauryl, myristoyl, palmitoyl and stearoyl.

The liposomes can be prepared from a mixture of dipalmitoylphosphatidyl choline and disteroylphosphatidyl choline in a weight ratio of 95:5 to about 5:95 and generally about 80:20 to about 20:80. In one embodiment, the liposomes are made from a mixture of dipalmitoylphosphatidyl choline and disteroylphosphatidyl choline in a ratio of 45:55 to about 55:45 provide a phase transition temperature of about 46° C. to about 49° C.

The liposomes of the invention can be prepared by standard processes as known in the art. The liposomes can be unilamellar or multilamellar and have a particle suitable for delivering the dye to the target site. In one embodiment, the liposomes have a particle size of a sufficiently small size to be introduced into the bloodstream of the patient in a location near the target site to flow through the target site.

The liposomes can contain a suitable osmotic pressure controlling agent that is physiologically acceptable to the patient. Examples include sodium chloride, sugars such as glucose, mannitol and sorbitol, and amino acids such as glycine, aspartic acid and glutamic acid. Examples of suitable process for preparing liposomes are disclosed in U.S. Pat. No. 4,235,871 to Papahadjopoulos et al. and U.S. Pat. No. 4,522,803 to Lenk, which are hereby incorporated by reference in their entirety.

The liposomes of the invention contain a dye that is able to fluoresce and that can be visualized in the target site by exciting with a light source that is amenable to the target site and the patient. The fluorescent dye can be any fluorescent that is suitable for encapsulation and is physiologically compatible. Preferably, the fluorescent dye is quenched when encapsulated at an appropriate concentration. The quenching concentration is a sufficiently high concentration to mask or minimize detection of fluorescence when illuminated by a fluorescing light source. The quenching concentration can be determined by routine experimentation as known in the art. When heated, the heat sensitive liposomes rupture or leak the dye and other components of the liposome so that the dye is diluted in the target site to a suitable concentration where the dye can be fluoresced and visualized upon excitation by a suitable light source. Examples of suitable dyes include 6-carboxyfluorescein and its derivatives. Suitable fluorescent dyes can be excited by an emit light at wavelengths that are not strongly absorbed by the tissue. Other suitable dyes include indocyanin green and aluminum phthalocyanine tetrasulfonate. It will be understood that the fluorescing light source and the visualizing instrument are selected according to the wavelength of the fluorescing dye to visualize the dye.

In one embodiment, the dye is selected to fluoresce in the presence of a light from an argon laser, a helium-neon laser or infrared laser. Preferably the dye is selected to be compatible with the exciting light or laser source to fluoresce when subjected to the light or laser beam. A suitable dye is sold under the tradename D-275 by Molecular Probes, Inc. and fluoresces green when exposed to light from an argon laser at 484 nm. A dye sold under the tradename D-1121 fluoresces orange when exposed to a long wavelength laser light at 560-574 nm. One preferred dye is an infrared excitable dye $Dilc_{18}(7)$, which fluoresces at a wavelength of 740-780 nm.

In one embodiment of the invention, a fluorescent dye is encapsulated in liposomes having a phase transition temperature of 42° C. to 50° C., and preferably about 45° C. to 49° C. In another embodiment, the liposomes have a phase transition temperature to release the dye at a temperature of about 46° C. to about 49° C. The liposomes are injected into the bloodstream of the patient in a location where the liposomes flow to the target site. In some embodiments, the liposomes can be introduced directly to the target site intravenously, subcutaneously or topically. A hyperthermal heat source and a dye exciting light source are applied to the target site. The hyperthermal heat source, which is preferably a laser light beam, is focused on the target site to heat the tissue and the cells to a temperature of at least 42° C. to hyperthermally treat the tissue and kill the cells. The hyperthermal heat source also heats the liposomes to a temperature at least equal to the phase transition temperature to release the dye. The fluorescing light source excites the dye so that the fluorescing dye in the target site can be detected and visualized. By encapsulating the fluorescent dye in liposomes having a phase transition of at least 42° C., the detection of the fluorescing dye provides a positive indication to the operator that the desired tissue temperature has been obtained that is necessary to hyperthermally treat the tissue. The phase transition temperature of the liposomes is selected according to desired minimum temperature that the tissue is to be heated. The hyperthermia energy source is applied to the target site for a time sufficient to treat the tissue to the desired level. Generally, the tissue is heated to a temperature of at least 42° C. for 1-15 minutes and preferably 1-10 minutes.

In one preferred embodiment of the invention, the liposomes contain a suitable drug or photosensitizing agent. The drugs preferably show a synergistic effect when combined with the hyperthermia treatment of the invention. The release of the drugs from the liposomes provide an improved targeting effect by releasing the drugs by the heat source in the target site. Suitable drugs include antitumor agents such as cisplatin, carboplatin, tetraplatin and iproplatin. Suitable anticancer drugs include adriamycin, mitomycin C, actinomycin, ansamitocin and its derivatives, bleomycin, Ara-C, daunomycin, metabolic antagonists such as 5-FU, methotrexate, isobutyl 5-fluoro-6-E-furfurylideneamino-xy-1,2,3,4,5,6hexahydro-2,4-dioxopyrimidine-5-carboxylate. Other antitumor agents include melpharan, mitoxantrone and lymphokines. The amount of the particular drug entrapped in the liposomes are selected according to the desired therapeutic dose and the unit dose.

Examples of suitable photosensitive (photosensitizer) agents include aminolevulinic acid, porphyrin derivatives, porpurine derivatives, NPE-6, ATX-10, plant derived photosensitizers. Other synthetic sensitizers such as $SNET_2$ and Lutex can be used. Preferably, the photosensitizers are used in non-toxic amounts. In other embodiments, the liposome compositions can contain liposomes that encapsulate a hyperthermic potentiating agent such as perfluorooctyliodide, perfluorotributylamine, perfluorotripropylamine, and perfluorooctylbromide. Examples of liposome encapsulated potentiators are disclosed in U.S. Pat. No. 5,149,319 to Unger, which is hereby incorporated by reference in its entirety. Other bioactive agents that can be delivered to the target site by encapsulating in liposomes include anti-inflammatory agents, antibiotics, antibacterial agents, antifungal agents, anti-neoplastic agents and antiparasitic agents. Examples of anti-neoplastic agents include aclacinomycins, chromycins and olivomycins.

In another embodiment of the invention, the liposome composition contains a mixture of liposomes having different phase transition temperature to release the components at different temperatures. In one embodiment, the liposome composition contains liposomes encapsulating a first dye and having a phase transition temperature of 42° C. to about 45° C. and liposomes encapsulating a second dye and having a phase transition temperature of about 50° C. or higher. In one embodiment, the second dye is encapsulated in liposome that release the dye at a temperature range of 50° C. to 60° C. Preferably, the second dye is able to fluoresce at different color than the first dye so that the dyes are distinguishable. In this embodiment, the liposome composition is delivered to the target and the target site is subjected to hyperthermia temperatures. As the tissue in the target site is heated to at least 42° C., the first liposomes rupture or release the first dye so that the first dye is visualized and detected in the target site. The detection of the first dye in the target site enables the operator to monitor the temperature of the tissue in the target site and to indicate that a hyperthermal temperature has been attained in the tissue at the target site. During hyperthermia, it is difficult to determine and monitor the actual temperature of the tissue and care must be taken to avoid overheating of the tissue and denaturization of the proteins. In preferred embodiments of the invention, the hyperthermal treatment does not exceed the protein denaturization temperature. In this embodiment, the second liposomes are selected to rupture or release the second dye at or slightly below the protein denaturization temperature. In this manner, the second dye is released and visualized to provide the operator with an indication that the tissue is heated to the protein denaturization temperature. The heat source is then adjusted by the operator to reduce the energy applied to the target site to avoid protein denaturization.

In another embodiment, the liposome composition can contain several liposomes that can leak or rupture at different temperatures to release the dyes at incremental temperatures as the temperature of the target site increases. In one embodiment, the liposomes can be selected to leak or rupture the dye at 2° C. intervals between about 42° C. and 50° C. The dyes for each liposome can be different to fluoresce a different color so that the different colors indicate a different temperature of the target site.

In other embodiments of the invention, the tissue in the target site can be irradiated by beta radiation from strontium or iridium isotopes. Gamma radiation from $P^{32}$, iodine-95, and palladium-90 can also be used. The radioactive isotopes can be delivered as small particles to the target site in combination with the hyperthermia treatment.

Another embodiment of the invention images the heat (temperature) production inside the eye (target) tissue. The desired temperature is achieved using a laser and photoacoustic imaging technique.

It is known that light can generate sound waves. This is the basis of photoacoustic technology. Some of the delivered energy, e.g., by laser, will be absorbed and converted into heat, leading to transient thermoelastic expansion and thus ultrasonic emission. The generated ultrasonic waves are then detected by ultrasonic transducers to form images. It is known that optical absorption is closely associated with physiologic properties, such as hemoglobin concentration and oxygen saturation. As a result, the magnitude of the ultrasonic emission, i.e., the photoacoustic signal, that is proportional to the local energy deposition, reveals physiological specific optical absorption contrast. Two- or three-dimensional images of the targeted tissues can then be formed.

A photoacoustic image is independently generated from an ultrasonic image, however, it is only visualized, i.e., imaged, by an ultrasonic receiver. Therefore, photoacoustic imaging and ultrasonic imaging should be performed simultaneously, so that the additional changes in the ultrasonic image, resulting from heat expansion, can be seen. In fact, if the ultrasonic wave and photoacoustic wave are parallel, there is no need for any other visualization system, as is the case is opaque tissue. The changes in the ultrasonic images are, however, dependent on the temperature that is created by an additional electromagnetic radiation, such as light, microwave generator, etc. This may be used when microwaves are used to treat intraocular tumors.

Presently, acoustically coupled resonant optical systems are sensitive enough to detect sound waves and differentiate the sound waves based on the temperature generated inside the target tissue. The pulsed light propagates in the ocular tissue uninterrupted until it meets the retino-choroidal tissue where it is differentially absorbed by the tissue producing a spatial distribution of the sound sources that can be imaged by an array of acoustic sensors. All visible light wavelengths and infrared wavelengths up to 1300 nm pass through the eye easily reaching the retina and choroids thus creating a high contrast between these tissue components. In the eye, most of retinal-choroidal pathology relates to the abnormal vessel formation, located at the junction of the retina and the choroids (new vessels), and most of the intraocular tumors are of retinal or choroidal origin permitting light, specifically infrared light at a wavelength of about 780 nm to about 1300 nm to penetrate these structures. The use of incoherent or partially coherent light permits penetration of a few centimeter and maintains a good spatial resolution for diagnosis or treatment. The ocular tissue, from the cornea to the retina, provide a uniform optical density and index of refraction. This index of refraction changes when the light reaches the retina and choroids. However, the contrast image, in ultrasonic imaging, is related to the density and compressibility of the tissue, not the index of refraction, thus permitting photoacoustic imaging to be used in evaluating functional properties of certain molecules based on different optical absorption of molecules, e.g. in oxymetry differentiating oxygenated and reduced hemoglobin.

The diagnostic application of photoacoustic imaging is based on the absorption of electromagnetic energy by different molecules, producing different changes in temperature, pressure, and density. Therefore, photoacoustic image generation is the result of photothermal effect on the tissue or molecules.

If the laser pulse is short enough, a local acoustic effect is generated that can be imaged by an ultrasonic transducer in 2D or 3D format. Because photoacoustic and ultrasonic imaging can share the same array and receiver, the image produced by them can simultaneously provide information on the thermal and anatomical structure, and location of the tissue in a rapid succession such as real time (video) images.

Nanosecond pulses can be generated from a Nd-YAG or Alexandrite laser. The laser delivery can be done either as a combined transducer-laser head or independently through any optical system such as a slit lamp, a direct or indirect ophthalmoscope, or a fundus camera. These instruments have their independent illuminations permitting simultaneous visualization or imaging of the lesion in the eye using multiple imaging modalities, potentially along the previously described markers such as liposomes. In this case, the ultrasonic images are obtained through an independent transducer.

A contrast agent or a marker (biomarker) can be used to enhance the image or temperature (heat production) in the growing cells, such as choroidal neovascularization or tumor cells. For example, gold nanoparticles or tubes can be injected systemically which has a light absorption around 800 nm wavelength, which corresponds to a laser often used in ophthalmology for retinal coagulation purposes. The contrast generated by the above biomarkers in photoacoustic imaging is proportional to the concentration of the biomarker. The gold nanoparticles may be any shape, e.g., spherical, ellipsoidal, tubular (cylindrical). The gold nanoparticles may be solid or hollow. The size of the gold nanoparticles may range from 2 nm to 700 nm. In one embodiment, the size of the gold nanoparticles ranges from 50 nm to 250 nm.

In one embodiment, the thermal images, generated using photoacoustic imaging, can indicate progressively increasing tissue temperature while the area is being treated. In one embodiment, a laser is used to treat the area while photoacoustic imaging is used to generate thermal images of the treatment area. In one embodiment, studies can be conducted to demonstrate the relationship between the photoacoustic images generated, as a result of a certain energy input, and incremental temperature rise in the tissue to create a target temperature, for example, up to 55° C., or any other temperature below the temperature of protein denaturation.

Upon injection of labeled gold nanoparticles, their concentration in the peripheral blood increases. The concentration is reduced within about 24 hours, depending in part on whether the gold nanoparticles contain (poly)ethylene glycol (PEG) groups or not (i.e., are PEGylated or not), because of hepatic clearance. The labeled gold nanoparticles are primarily either present in a bound form, e.g., an antibody-labeled-nanoparticle-cell (malignant cell) complex, or are absorbed by the tumor cells and hence are internalized. Hence, their decreased concentration in peripheral blood (e.g., blood sample obtained by venipuncture) indicates presence of a tumor cell, and provides quantitative information about the number of labeled cells per ml blood. Subsequently the total number of circulating cells in the total whole blood volume of a patient can be calculated. This permits discovery the presence of malignant cells, the ability to quantify the amount of circulating malignant cells from one lesion or multiple metastatic lesions which have metastasized, and to obtain information on their locations in the body.

Obtaining blood samples over a period of time (hours, days, weeks, etc.) and subsequently measuring the concentration of the labeled particles, indicates an increase or decrease in tumor cell shedding as a result of any therapy such as radiation, chemotherapy, thermotherapy, etc. It is thus of diagnostic usefulness, e.g., to monitor efficacy of therapy in a patient receiving therapy for a tumor. The patient receives an intravenous injection of a defined concentration of labeled gold nanoparticles. The concentration of the labeled nanoparticles in the peripheral blood is determined; this is a base level. Then, at a defined interval (e.g., days, weeks, etc.), as determined by a health professional, another peripheral blood concentration of the labeled nanoparticles is determined as an indicator of labeled nanoparticle clearance from the peripheral blood. The decrease in nanoparticle concentration is determined, and correlated with the previous uptake to determine the presence of a tumor, absence of a tumor, or decreased tumor burden (shedding). To illustrate, e.g., a decrease up to 30% to over 95% in 7 days indicates normal clearance of the labeled nanoparticles, and a decrease up to 99% over 7 days to 14 days indicates internalization of the labeled nanoparticles by a tumor. Any significant detection of nanoparticles beyond this time period indicates presence of circulating tumor cells; confirmation is obtained by evaluating a peripheral blood sample obtained by venipuncture and/or by tumor cell histological examination.

In embodiments, the gold nanoparticles can be injected into a tumor, injected into a body cavity, applied over a mucosal surface, and/or applied to skin having a tumor. The absorption of the labeled particles can be used to differentiate a benign tumor from a malignant tumor and simultaneously to treat the tumor by the disclosed method of thermotherapy. In malignant tumors, the gold nanoparticles coated with anti-tumor antibody are absorbed by the tumor and remain in the tissue. In benign tumors, the gold nanoparticles coated with anti-tumor antibody may be initially absorbed by the tumor, but will not remain in the tissue and after 1-2 days are eliminated by systemic absorption.

In other embodiments, nanoparticles of a material other than gold may be used. These include, without limitation, diamond nanoparticles, platinum nanoparticles, combinations of gold, platinum, and/or diamond nanoparticles. Any of the above nanoparticles may contain at least one hydroxyl group. All such nanoparticles provide the various diagnostic and therapeutic applications as described above for gold nanoparticles. The sizes and shapes are the same as those described for gold nanoparticles. All such nanoparticles may be covalently attached to (poly)ethyleneglycol, i.e., may be PEGylated.

All such nanoparticles create photoacoustic waves when exposed to an external energy source such as light, ultrasound, lasers, radiation, microwave, etc. The temperature of the nanoparticles rises and their molecules expand. Molecular expansion produces an acoustic sound that can be recorded as a photoacoustic wave signal from an in vivo or in vitro environment. These sounds, photoacoustic signals, are received by acoustic wave detectors or sensors, and are recorded and analyzed. Such methods are known in the art and are similar to signals obtained by endogenous chromophores such as hemoglobin. However, because the gold nanoparticles have stronger absorption of the radiation than other chromophores, e.g., 30% to 99% higher, less energy is required to generate an appropriate signal. The signals of each chromophore can also be differentiated from other signals by ultrasonic spectroscopy. Acoustic wave sensors have acoustic wave resonator elements including piezoelectric material (elements), as known by one skilled in the art. This ability to create and record the acoustic signal is useful for treating tumors, monitoring treatment efficacy, and making diagnoses, distinguishing malignant cells from benign cells, etc. in the same way as previously described for optical tissue. For example, the absence of malignant cells does not generate an image in photoacoustic imaging, and generates a different acoustic signature or characteristic in ultrasound spectroscopy. Thus, the method can evaluate the presence or absence of malignant cells in a human patient. An antitumor antibody-labeled nanoparticle, and a temperature indicating substance, in administered to the patient to form an antibody-labeled-nanoparticle-cell complex at the tumor site. Then, the tumor site is exposed to a radiation energy source under conditions sufficient to achieve a temperature of the complex between 41° C. to 56° C. The acoustic sound produced from the nanoparticle at the site is evaluated and correlated with the presence or absence of malignant cells at the target site by photoacoustic imaging and/or ultrasound spectroscopy.

One embodiment using the above-described labeled nanoparticles is a method to differentiate a tumor or lesion containing malignant cells from one containing benign cells. The nanoparticles are coated with a targeting agent, e.g., antibodies other identifiers known to one skilled in the art, such that they target specific cells when intravenously injected or otherwise administered into a patient.

Cells that are labeled or tagged with gold nanoparticles show 30-40% increase in the resultant acoustic signal, compared to the untagged cells if the cells possess pigmentation. However, a sample of blood or other tissue, or a tumor (e.g., from biopsy) may be obtained and then bleached in vitro to rid the cell of pigment, e.g. melanoma cells. The samples are exposed to an external energy source (light, laser, etc) and the resulting photoacoustic wave signals are measured and analyzed using an ultrasonic spectrometer or other comparable device to determine the presence or absence of the malignant cells. The bleaching step is not needed for the majority of the neoplasms to generate photoacoustic signals, e.g., between a normal cell versus one tagged with gold nanoparticles. to be significant. The differences in the optical absorption of, e.g., light energy, permits differentiation, in vivo and in vitro, between normal and metastatic lesions (tumor cells).

In vitro acoustic cell analysis is performed by taking a biological sample from a patient, e.g., a known volume of blood or other body fluid that may contain circulating malignant cells, e.g., cerebrospinal fluid (CNS), lymphatic fluid, etc. To this fluid sample is added a specific antibody-coated gold nanoparticle. Because of the specificity of the antibody to a particular cellular receptor, protein, or other binding target, the gold nanoparticle binds to the specific cells present in the fluid and is detected, quantitated, monitored, etc. In one embodiment, an optional temperature-indicating substance is added for in vitro evaluation of the circulating tumor cells in the absence of nanoparticle injection. This is useful to indicate is metastatic cells are being released, because a positive result can initiate a search for potential metastatic lesions even if they have not progressed to a size so as to be visible by standard means of examination such as computed tomography (CT) or magnetic resonance imaging (MRI). The sensitivity threshold of recognizing a metastatic lesion is greater than about 1 mm diameter tumor, compared to a sensitivity threshold of greater than about 10 mm diameter tumor with standard means of examination. In either embodiment, the fluid is then analyzed by, e.g., an ultrasonic spectrophotometer or another appropriate device, to measure the number of tagged cells in the fluid. This procedure and analysis can also be adapted for use for other types of body sample such as tissue biopsies as known to one skilled in the art.

In one embodiment, a patient-specific antibody to a tumor is prepared. After biopsy, a specific antibody to the malignant cells of the tumor is generated. The antibody is then coated with gold nanoparticles resulting in an antitumor antibody-labeled nanoparticle. In one embodiment, a biphasic antibody that binds a target via its Fab region is prepared. In one embodiment, an antibody that binds a target via its Fc region is prepared. Such procedures are known to one skilled in the art. These antibody-coated nanoparticles are specific for a specific tumor cell present in the patient forming an antitumor antibody-labeled nanoparticle-cell complex. In one embodiment, the complex may contain a compound, e.g., an antivascular endothelial growth factor and/or an antiproliferative agent. In one embodiment, the antibodies may also be labeled with a fluorescent dye.

As known to one skilled in the art, tumor cell membranes contain numerous receptors. In one embodiment, multiple antibodies against individual antigens may be generated from a tissue biopsy sample. Coating various gold nanoparticles with specific antibody against the tumor cell permits treating a single tumor cells with multiple gold nanoparticles, either alone or with conventional chemotherapy and/or radiation therapy, thus enhancing the tumor-destroying potential of the method. In one embodiment, the combination of targeted hyperthermia plus radiation, etc. provides conditions in which lower than typical levels of radiation are needed to destroy tumors, reducing radiation side-effects.

The above in vitro method and analysis can also be used to determine the temperature (energy) needed to kill tagged malignant cells, or other cells of interest, without damaging the surrounding normal cells. This parameter is incorporated in an in vivo procedure to treat specific tumor or circulating malignant cells. For example, a tumor cell lacking pigmentation (e.g., breast cancer cells) may be killed using lower energy levels than a tumor cell having pigmentation (e.g., melanoma cells).

In one embodiment, a collar positionable to fit on or around a patient's neck or extremities, contains a multiple diode laser that emits specific wavelengths of radiation energy to heat the labeled nanoparticles to a temperature sufficient to thermally destroy the tumor cells and they circulate in the area encompassed by the collar. Other devices that can be used outside or implanted in the body as known to one skilled in the art may incorporate the method for treating and/or destroying malignant cells within other compromised areas of the body such as those having tumors. Because the temperature generated inside the cells tagged with gold particles exceeds that of exposed non-tagged normal cells, this method protects normal cells while damaging the malignant cells.

In one embodiment, the method uses magnetic energy to provide the hyperthermal treatment. This embodiment is used for applying hyperthermal treatment to a lesion that is not accessible to application of light energy. Examples of such inaccessible lesions include brain cells, or cells deep inside the body.

In this embodiment, magnetic nanoparticles are used. In one embodiment, ferromagnetic, e.g., iron oxide, nanoparticles are used, either alone or combined with other magnetic materials or paramagnetic materials such as tungsten, cesium, aluminum, lithium, manganese, sodium, platinum, and oxygen. Such magnetic nanoparticles are provided to a patient and exposed to an energy source that provides a magnetic field (e.g., coil, wire) that reverses the direction of the field rapidly using alternating current. In one embodiment, the particles are injected locally, e.g., inside a tumor. In one embodiment, the particles are administered intravenously. In one embodiment, the particles are both injected locally and administered intravenously. The particles heat up and expand, producing detectable acoustic (sound) waves. The magnetic field ranges from about 0.0001 Tesla (T) to about 3 T. The degree of heat produced upon such exposure induce an expansion of the nanoparticles that is recorded by an ultrasonic transducer, as previously described.

The magnetic particles are attached to an antibody, as previously described, forming ferromagnetic-antitumor antibody-labeled nanoparticles. These particles provide diagnostic and/or therapeutic thermal heating at a biological target or lesion. A temperature indicating substance is also labeled with the antibody of interest, the ferromagnetic particle, or a combination of both.

As one example, a solution or formulation containing the ferromagnetic-antibody labeled nanoparticles is administered by injection to a human or animal patient or by topical application. The antibody, upon binding to its cellular target, forms a ferromagnetic-antibody labeled nanoparticle-cell complex. After a period of time to allow clearance of the unbound ferromagnetic particles from the patient, the patient is placed in a magnetic field. In one embodiment, this clearance time is less than 2 hours. In one embodiment, this clearance time is 2 hours. In one embodiment, this clearance time ranges between 24 hours to 48 hours. In one embodiment, this clearance time is up to 48 hours. In one embodiment, this clearance time is greater than 48 hours.

Clearance can be assessed the determining the presence of circulating nanoparticles in the patient. as follows. A small volume of patient's blood is placed inside a small electric coil (0.0001 T-0.1 T) in vitro. Altering the magnetic field heats the particles and generates photoacoustic images measured by the ultrasonic transducer, which indicates the present of circulating nanoparticles. The pharmacokinetic of these circulating particles can be measured. When the level of circulating nanoparticles are significantly reduced as described previously, e.g., 2 hours-24 hours post injection, the patient is positioned inside an a magnetic resonance imaging (MRI) instrument or any other applicable instrument known to one skilled in the art.

The applied magnetic field heats the nanoparticles, including the sessile or attached particles to the tumor. The procedure is automatically controlled by photoacoustic imaging monitoring, as subsequently described below. The degree of heat production in the particles induces an expansion of the nanoparticles that is recorded by an ultrasonic transducer previously described. The patient is maintained in the magnetic field until a diagnostic or therapeutic temperature of 42° C. to 56° C. is reached. The time to reach this temperature depends upon the energy applied in one session. The session can be repeated as desired. Generally, the exposure time may vary from <1 minute to >10 minutes. The acoustic sound produced from the nanoparticle at the site is evaluated and correlated with the presence or absence of malignant cells at the target site by photoacoustic imaging and/or ultrasound spectroscopy. A photoacoustic image is created by exposing the tissue or site to electromagnetic radiation, e.g. 190 nm microwave and radiofrequency using a laser. If the material has magnetic properties, by reversal of the magnetic field, one can heat the tissue or site; one can also use mechanical waves produced by another ultrasound transducer to heat the tissue or site. These mechanisms create thermoelastic expansion of a molecule that generates a wideband (MHz) emission. The time and amplitude of the photoacoustic images provide information regarding the absorption and location of the source, depending on the degree of thermal expansion of the material, etc., as known to one skilled in the art.

In one embodiment, the method uses magnetic energy to provide the hyperthermal treatment. This embodiment is used for applying hyperthermal treatment to a lesion that is not accessible to application of light energy. Examples of such inaccessible lesions include brain cells, or cells deep inside the body.

In this embodiment, magnetic nanoparticles are used. In one embodiment, ferromagnetic, e.g., iron oxide, nanoparticles are used, either alone or combined with other magnetic or paramagnetic materials. Such magnetic nanoparticles are provided to a patient and exposed to an energy source that provides a magnetic field (e.g., coil, wire) that reverses the direction of the field rapidly using alternating current.

The following methods control the energy applied to the nanoparticles, indicating when to treat after injection of the nanoparticles. A noncoagulative laser or radiofrequency or an acoustic wave, when absorbed, can produce a photoacoustic ultrasonic emission of about 1 MHz or more (two- or three-dimensional), creating an image of a tissue, site, etc. The image, in the form of a graph, curve, etc, shows an amplitude that depends on the amount of thermal energy absorbed or produced at the tissue or site. One can record this temperature increase as an image, regardless of the exact degree increase. This characteristic can be used to distinguish low and high energy applied, e.g. internally generated, by magnetic resonance on the ferromagnetic particles, and can be used to modify the amount of energy required. A computer processor (digital signal processor) can transmit the desired signal from the ultrasound unit to a device, e.g., a laser, radiofrequency device, magnet, etc., as known to one skilled in the art, to increase or decrease the applied energy to achieve potentially any desired temperature for any given situation and site. This energy varies; relatively low heat up to 55° C. for non-coagulative laser treatment, to >60° C. for coagulative laser treatment, to >100° C. in one embodiment and >500° C. in one embodiment for photoablative laser treatment, i.e., very short pulses but very high energy, depending on how deep the target tissue is located inside the body, and the property of the energy absorber inside that targeted tissue. This method results in a treatment that is visible, adjustable, and automatic depending on the needed temperature regardless of the depth of the lesion inside the body. Previously only a light source with an external photographic device could indicate the surface temperature. However these devices and wavelengths are limited by their wavelength, tissue penetration, and tissue water content, limiting light transmission to a few millimeters.

Photoacoustic spectroscopy is very sensitive if a tissue contains any gas. Because animal tissue always contains gases as oxygen, nitrogen, and/or carbon dioxide, any degree of temperature increase causes expansion of these gases at that location. The sensitivity of photoacoustic spectroscopy can reach one part in trillion levels. Therefore this method demonstrates the thermal effect that was generated on the specific tissue, and the energy-absorbing nanoparticles can be imaged inside the body using this method.

As one example, a solution or formulation containing the ferromagnetic-antibody labeled nanoparticles is administered by injection to a human or animal patient human patient. The antibody, upon binding to its cellular target, forms a ferromagnetic-antibody labeled nanoparticle-cell complex. After a period of time, such as at least 2 hours up to 48 hours or more to allow clearance of the unbound ferromagnetic particles from the patient, the patient is placed in a magnetic field, such as that provided by an magnetic resonance imaging instrument or any other applicable instrument known to one skilled in the art. The applied magnetic field heats the nanoparticles. The degree of heat production in the particles induces an expansion of the nanoparticles that is recorded by an ultrasonic transducer previously described. The patient is maintained in the magnetic field until a diagnostic or therapeutic temperature of 42° C. to 56° C. is reached. The heat production is controlled to achieve this temperature and hence to treat only tumor cells. The acoustic sound produced from the nanoparticle at the site is evaluated and correlated with the presence or absence of malignant cells at the target site by photoacoustic imaging and/or ultrasound spectroscopy.

Although several embodiments have been chosen to illustrate the invention, those skilled in the art will readily appreciate that various changes and modifications can be made without departing from the scope of the invention.

What is claimed is:

1. A method of diagnosing and hyperthermally treating malignant cells in a patient, the method comprising
    injecting a ferromagnetic-antitumor antibody labeled nanoparticle and a temperature indicating substance to form an ferromagnetic-antibody labeled nanoparticle-cell complex at a target site,
    exposing the target site to a magnetic field energy source under conditions sufficient to heat the ferromagnetic particles in the nanoparticle-cell complex to a temperature between 42° C. to 55° C.,
    measuring the acoustic response produced by the nanopaticles, and
    determining the presence or absence of malignant cells at the target site based on the nanoparticle acoustic response,
the ferromagnetic nanoparticles comprising iron oxide.

2. A method of diagnosing and hyperthermally treating malignant cells in a patient, the method comprising
    injecting a ferromagnetic-antitumor antibody labeled nanoparticle and a temperature indicating substance to form an ferromagnetic-antibody labeled nanoparticle-cell complex at a target site,
    exposing the target site to a magnetic field energy source under conditions sufficient to heat the ferromagnetic particles in the nanoparticle-cell complex to a temperature between 42° C. to 55° C.,
    measuring the acoustic response produced by the nanopaticles, and determining the presence or absence of malignant cells at the target site based on the nanoparticle acoustic response;

wherein the magnetic field energy source is a magnetic resonance imaging instrument.

3. A method of diagnosing and hyperthermally treating malignant cells in a patient, the method comprising injecting a ferromagnetic-antitumor antibody labeled nanoparticle and a temperature indicating substance to form an ferromagnetic-antibody labeled nanoparticle-cell complex at a target site, exposing the target site to a magnetic field energy source under conditions sufficient to heat the ferromagnetic particles in the nanoparticle-cell complex to a temperature between 42° C. to 55° C., measuring the acoustic response produced by the nanopaticles, and determining the presence or absence of malignant cells at the target site based on the nanoparticle acoustic response;

where the magnetic field ranges from 0.0001 Tesla (T) to 3 T.

* * * * *